United States Patent [19]

Jacobsen

[11] 3,935,463

[45] Jan. 27, 1976

[54] SPECTROPHOTOMETER

[75] Inventor: John Kenneth Jacobsen, Madeira Beach, Fla.

[73] Assignee: Milton Roy Company, St. Petersburg, Fla.

[22] Filed: Dec. 5, 1974

[21] Appl. No.: 529,838

[52] U.S. Cl. ............... 250/373; 250/365; 250/238; 350/61; 356/51; 356/207
[51] Int. Cl.² ..... G01J 3/00; G01J 3/46; G01J 5/56; G01N 21/26
[58] Field of Search ........... 250/365, 364, 238, 373; 356/207, 51; 350/61

[56] References Cited
UNITED STATES PATENTS

| | | | |
|---|---|---|---|
| 2,411,672 | 11/1946 | VanDenAkker | 250/373 |
| 3,731,091 | 5/1973 | Rosso et al. | 250/373 |
| 3,778,162 | 12/1973 | Gant et al. | 356/51 |
| 3,819,945 | 6/1974 | Egan et al. | 250/373 |
| 3,861,802 | 1/1975 | Belmear, Jr. | 350/61 |

FOREIGN PATENTS OR APPLICATIONS

| | | | |
|---|---|---|---|
| 1,243,005 | 6/1967 | Germany | 350/61 |

*Primary Examiner*—James W. Lawrence
*Assistant Examiner*—T. N. Grigsby
*Attorney, Agent, or Firm*—Woodcock, Washburn, Kurtz & Mackiewicz

[57] ABSTRACT

An improved spectrophotometer of the non-dispersive absorption type useful for detecting the presence of $SO_2$ in a gaseous sample, despite the simultaneous presence of $NO_2$. Ultraviolet light from a commercially-available source impinges upon a fixed phosphor screen which fluoresces to produce ultraviolet radiation at a first wavelength, at which both $SO_2$ and $NO_2$ absorb radiation; and at a second wavelength at which absorption by $SO_2$ is minimal but $NO_2$ absorption is approximately the same as at the first wavelength. The radiation is directed through a sample chamber having windows which are transversely slidable to effect cleaning without destroying the integrity of the chamber seal, then introduced into an envelope enclosing filters and a pair of photosensors. One photosensor receives light at the second wavelength and produces a signal which reflects the attenuation by $NO_2$ at that wavelength. The other sensor has disposed in front thereof a filter for blocking the second wavelength, and passing the first; and a phosphor for converting the passed (first) wavelength radiation into radiation at the second wavelength, which is then detected to produce a measure of the combined effect of $NO_2$ and $SO_2$. A comparison circuit then detects the differential between the first and second photosensors to determine the concentration of $SO_2$. Means are provided to maintain the lamp, sample chamber and envelope at predetermined temperatures. A source of mercury vapor within the envelope saturates the interior of the envelope with the vapor for selectively attenuating undesired radiation at the 254 wavelength.

25 Claims, 4 Drawing Figures

SPECTROPHOTOMETER

BACKGROUND OF THE INVENTION

The present invention relates to spectrometry, and more specifically to a non-dispersive spectrophotometer adapted to detect the presence of $SO_2$ in a sample, regardless of the presence therein of $NO_2$.

It is a well-known phenomenon that the atoms or molecules of a given material may absorb electromagnetic radiation at specific frequencies, the frequencies and relative intensity of the radiation absorption comprising the spectral "signature" of the material. This characteristic may be utilized to identify the presence of a given material by directing radiation upon it, and noting the degree and/or wavelength at which the radiation is attenuated.

In recent years the urgency of controlling, and indeed reducing, the incidence of pollutants in the atmosphere has become apparent. Long-known apparatus have been modernized, and new apparatus devised, in order to meet stringent requirements placed upon both government and industry for controlling and lessening the output of pollutants including those transferred to the atmosphere by smoke, flue gases, and other vaporous effluences from industrial and other processes.

In order to monitor the operation of these devices, and to detect the presence of certain specified polluting agents, analytical apparatus is needed. Although various types of apparatus have long been known they have typically taken the form of laboratory apparatus which, though highly accurate, are very expensive and often ill-suited for day-to-day usage in an industrial environment, often by semi-skilled personnel.

Many efforts have been directed toward the provision of pollution detecting apparatus which fulfill the above-described need. Any one of a number of physical principles may be utilized to achieve the desired analysis; conductometric, colormetric, coulemetric, electrochemical transducers, photoemission, flame photometric, thermoconductivity, infared, and ultraviolet light absorption of both the dispersive and non-dispersive types are available, and have long been known in the art. Of all the foregoing approaches, the one which is believed to show the most promise for fulfilling commercial needs is the ultraviolet absorption type. In U.S. Pat. No. 2,350,001-Van Den Akker, for instance, a recording device is shown which utilizes the spectral absorbing properties of a gas or vapor to detect its presence. An ultraviolet light source has its beam split into two elements, which traverse two physically separate paths or channels; suitable filter means is used to selectively attenuate the radiation to facilitate the process. In one embodiment, a fluorescent plate is used to obtain light at a predetermined wavelength in response to the impingment thereon of ultraviolet light at a second wavelength. U.S. Pat. No. 3,778,162-Gant et al discloses means for measuring the amount of mercury vapor present in a sample and uses a pair of channels for comparing the transmission of ultraviolet light, one of said channels having therein a reservoir of mercury vapor. U.S. Pat. No. 3,819,945-Egan et al teaches a spectrometer for detecting the presence of nitric oxide (NO) by identifying a portion of its spectral signature. Mechanical choppers are used for periodically interrupting a beam of impingent light and a grating diffracts the light, spreading it into a spectrum so that predetermined wavelengths thereof may be selected by means of a mechanical shutter. The foregoing approaches, while presumably effective, nonetheless have the deficiency of being expensive and/or complex.

The present invention teaches an improved spectrometer for analyzing a gaseous sample particularly for the presence of $SO_2$ through the use of a two-channel approach; but without the need for an expensive redundant system of lenses, sample chambers, etc. Further, with the approach taught herein, a selected material may be identified by its spectral absorption characteristics without the need for diffraction gratings, movable shutters, mechanical choppers, and the like. Moreover, the foregoing desideratum is achieved with the use of a relatively inexpensive, commercially available light source.

It will therefore be understood that one object of the present invention is to provide an improved gaseous analyzer of the non-dispersive, absorption type.

It is another object of the present invention to provide a practical spectrophotometer which is substantially simpler in operation than those heretofore known.

Still another object of this invention is to provide an improved spectrophotometer analyzer which can be inexpensively constructed yet has the precision necessary for identifying undesirable levels of a specified pollutant.

SUMMARY OF THE INVENTION

Briefly stated, in accordance with one aspect of the invention the foregoing objects are achieved by providing a radiation source which comprises a lamp and a phosphor screen for producing radiation at first and second specified wavelengths. A pair of photosensors are disposed in a sealed envelope in spaced relationship to the source and a sample chamber is interposed between the source and the envelope. Suitable filters are provided such that the second one of the photosensors receives that radiation having the second wavelength. A filter disposed between the chamber and the first photosensor selectively blocks radiation of the second wavelength, while passing that at the first wavelength. A phosphor screen converts the radiation at the first wavelength back to the second and transmits it to the first photosensor.

The first wavelength is selected to correspond to one at which the material sought to be identified exhibits strong absorption characteristics. The second wavelength is selected to occur at a point where a second material which may also be present, absorbs at a rate equal to its absorption at the second wavelength. Circuitry is provided for comparing the responses of the two photosensors, the differential therebetween reflecting the presence of the material sought to be identified.

In a preferred embodiment, opposite ends of the sample chamber have elongate panes provided therein and encaptured within gaskets which allow the panes to be transversely displaced without destroying the integrity of the seal of the chamber. In order to attenuate energy at an undesired spurious wavelength a source of metallic vapor is disposed within the aforementioned envelope, the vapor having an absorption line corresponding to the wavelength of the undesired radiation. Finally, the combination of a temperature detector and a heating element is associated with each of the lamp, sample chamber and envelope, each temperature detector being coupled to control circuitry which energizes the heating element to maintain the temperatures of the respective lamp, sample chamber and envelope at selected levels.

BRIEF DESCRIPTION OF THE DRAWINGS

While the specification concludes with claims particularly pointing out and distinctly claiming the subject matter which is regarded as the invention, it is believed that the invention will be better understood from the following description of a preferred embodiment taken in conjunction with the accompanying drawings which:

DESCRIPTION OF A PREFERRED EMBODIMENT

Figure 1:
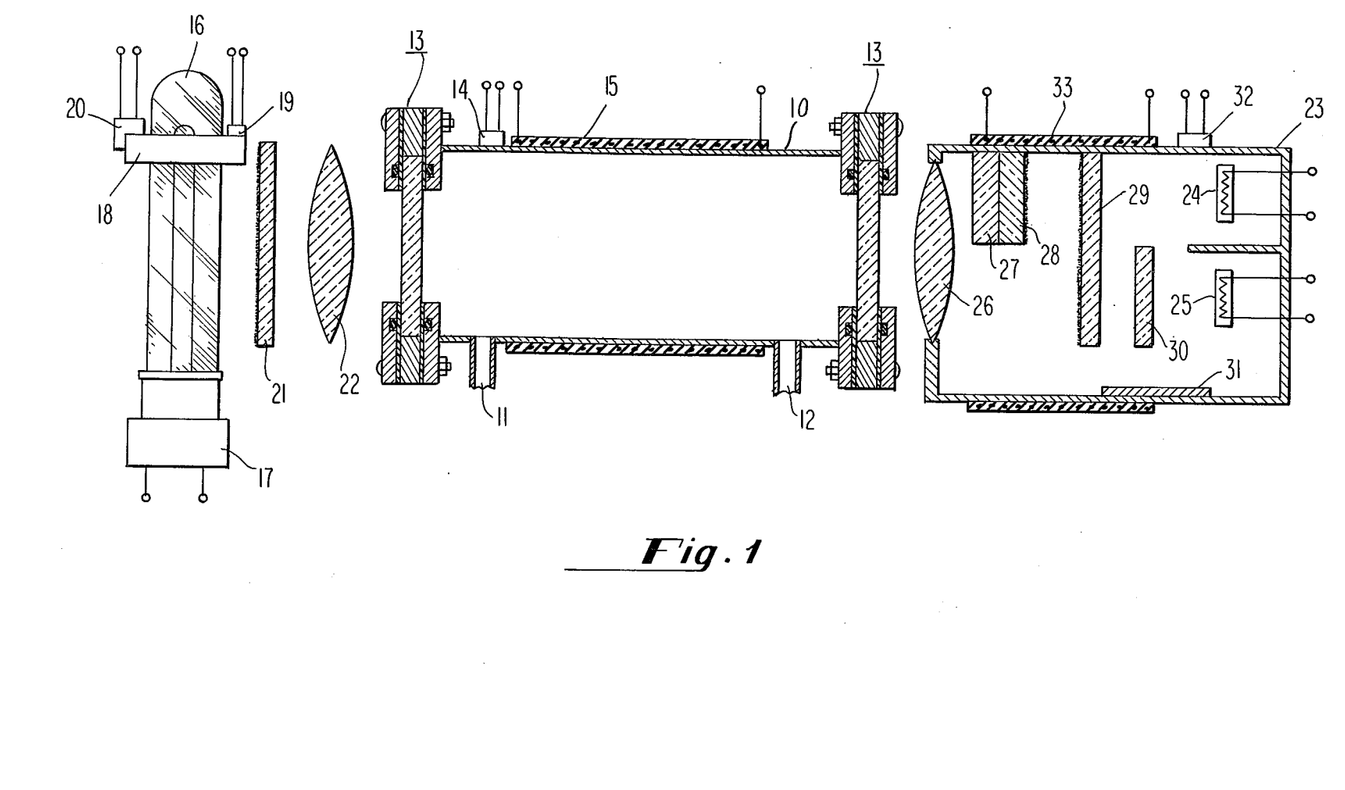
FIG. 1 is a partial cut-away side elevation illustrating important elements of the present system.

FIG. 1 shows, in cutaway form, principle elements of a spectrophotometer constructed in accordance with the teachings of the present invention. A sample chamber 10 is provided with an inlet 11 and outlet 12 to allow the introduction and exhausting of a gaseous sample to be analyzed. The chamber may be constructed of a suitable material such as stainless steel, and has affixed at both ends thereof a window assembly generally designated 13. A heat detector 14, which may be a thermistor, is intimately associated with the wall of the chamber and is coupled to control apparatus (not shown) to maintain the temperature of the chamber within predetermined limits. A heating element 15 is disposed about chamber 10, and coupled to a source of electrical energy. The flow of current through heater 15 is varied in response to the condition of thermistor 14, in order to maintain the temperature within sample chamber 10 at a predetermined level.

It has been found that a temperature of 250°F is suitable, preventing the condensation of any water present in the sample which would absorb an undue amount of $SO_2$ and distort the results of the analysis. Heater 15 is advantageously of the resistive type and comprises a network of resistive wires imbedded in a flexible material, such as silicone rubber, which is disposed about the periphery of chamber 10.

The necessary ultraviolet radiation is obtained from a lamp generally designated at 16. Lamp 16 is advantageously mounted on block 18 which serves as a heat sink. A resistive heating element, shown in idealized form at 20, is also coupled to the heat sink and receives current from a source of electrical energy which is controlled in response to the status of thermistor 19. In this manner, heat may be transferred to the lamp as needed to maintain it at a predetermined temperature. By closely controlling the temperature of the lamp the spectral characteristics of the radiation produced thereby may be maintained at a predetermined value, avoiding the necessity for the continuing adjustment of subsequent radiation sensing apparatus.

Disposed between lamp 16 and sample chamber 10 is a phosphor element 21. Element 21 advantageously comprises a sheet of quartz having disposed thereon a combination of phosphors responsive to the incidence of 254nm radiation to re-radiate ultraviolet radiation at wavelengths of both 280 and 540nm. In a preferred embodiment approximately 80% of the phosphor utilized comprises Type X-401 lanthanum fluoride phosphor, obtainable from General Electric Co., and which strongly emits radiation at between 275 and 310nm; and 20% of a standard phosphor having JEDEC designation P1, obtainable from the Sylvania Electric Co. and which emits radiation at between 510 and 560nm. The ultraviolet radiation produced by phosphor screen 21 may advantageously be collected and collimated by a quartz lens 22.

Since lamp 16 is a relatively inexpensive, commercial grade device it will be understood that the radiation produced thereby contains more spurious wavelengths than would be present in an expensive, laboratory device. In using the lamp referred to above it has been found that in addition to the 254nm wavelength, radiation at 360nm and also some spurious infrared radiation are produced. No attempt to attenuate these wavelengths is made precedent to their entering the sample chamber, suitable filtering means being subsequently provided as will be described hereinafter. The radiation emanating from, or passing through, phosphor screen 21 and lens 22 then traverses the pane of the adjacent window means and traverses the gaseous sample within test chamber 10, emerging at the other end thereof through the pane of the opposite window means. While the panes may be made of any suitable material, it has been found that a planar element of quartz is well suited to the task.

Adjacent the distal end of the sample chamber from the source is an envelope 23 which sealingly encloses means responsive to the radiation emanating from lamp 16. The first and second photosensors 24, 25 are advantageously matched so that subsequent balancing circuitry is unnecessary. Such matched pairs of photosensors are commonly packaged upon a single substrate and are available from many commercial sources. In a preferred form of the invention these photosensors are principally responsive to radiation at either 280nm or 540nm; in the disclosed embodiment they are responsive to a wavelength of substantially 540nm. An opening in envelope 23 is sealingly closed by lens 26, which further collects the radiation issuing from window means 13 and directs it to the photosensors.

While the radiation issuing from lamp 16 has thus far been treated as a single entity or beam, in order to facilitate the operation of the present invention two separate paths or channels are provided for its receipt within envelope 23. In a first path, the serial combination of an ultraviolet filter 27 and a phosphor screen 28 are disposed behind one portion of lens 26, and in front of photosensor 24. Filter 27 is selected to have a characteristic of transmitting only the ultraviolet portion of that radiation which it receives from sample chamber. The phosphor is excited principally by ultraviolet radiation in the 280nm range, and emits radiation in response thereto at a wavelength of substantially 540nm. Thus, the radiation appearing before photocell 24 has a wavelength of substantially 540nm, but reflects the presence of only 280nm radiation in the sample chamber. The 360nm radiation outputted by lamp 16 and which traverses the sample chamber is not effective to cause re-radiation by phosphor 28, and is substantially attenuated.

Disposed in front of both photosensors 24 and 25 is a common filter 29 which in one successfully-tested embodiment comprised a Wratten no. 57 filter manufactured by the Eastman Kodak Co. of Rochester, N.Y. Filter 29 blocks unwanted blue, red and infared radiation from impinging upon photosensors 24 and 25. The filter is advantageously coated with a film composed of a solution of an appropriate ultraviolet light absorber such as that marketed under the trade name of Cyasorb 9. This material absorbs ultraviolet light and prevents it from bleaching filter 29. Disposed directly behind filter 29, and in front of photosensor 25 is a second filter 30 such as a Wratten no. 65 filter which serves to absorb spurious 546nm radiation, and acts as a relatively narrow band-pass filter to allow only the desired 540nm radiation to pass.

Also disposed within envelope 23 is a segment 31 of a material such as copper or brass which has amalgamated into the surface thereof a quantity of mercury. As will be understood by those skilled in the art, the mercury vaporizes within the envelope until the vapor achieves saturation of the atmosphere therewithin, according to the ambient temperature of the interior of the envelope. The mercury vapor serves as a selective filter to attenuate any stray 254nm radiation which has traversed the sample chamber and entered the envelope. Although it is known in the art to provide a mercury vapor filter comprising a sealed envelope of mercury vapor and disposed in the path of ultraviolet radiation, the addition of such an envelope to the present apparatus would necessarily enlarge it considerably, and complicate its construction. Further, the expense of providing such a cell within envelope 23 would add an undesirable feature to the apparatus.

The inventor has found that in practice the mercury vapor does not coat or condense upon filters, lenses, or photocells and render them inoperative. Rather, as the temperature within the envelope declines the tendency of the mercury is to be re-combined with the amalgamated surface of segment 31. The amalgamated material and the sealed envelope thus combine to form an efficient yet inexpensive auxiliary filter which acts in concert with the already-present filter elements to selectively attenuate unwanted radiation.

In order to maintain envelope 23 and its contents at a proper temperature a thermal sensing device such as thermistor 32 is disposed in close communication with the envelope. A heating element 33, advantageously of the above-described resistive heating type, is formed about the periphery of the envelope 23 and coupled to a source of current which is varied by suitable control circuitry in response to the status of heat sensing element 32. While the temperature of the envelope is not critical, in practice it has been found advantageous to maintain it at approximately 130°F.

The operation of the invention as depicted in FIG. 1 will now be described, making particular reference the elements of the Figure enumerated above. When it is decided to analyze a sample for the presence of a suspected pollutant, i.e. $SO_2$, a sample is introduced into chamber 10 through conduit 11. At the same time the material previously within the chamber is exhausted through opening 12. Lamp 16 is energized, producing radiation principally at 360 and 254nm. The radiation thus produced is directed against phosphor screen 21, the constituents of which are excited by the 254nm radiation and fluoresce to produce radiation at wavelengths of both 280 and 540nm.

The selection of the latter wavelengths arises due to the spectral signature of $SO_2$ and that of another material commonly encountered, $NO_2$. While $SO_2$ has a marked absorption occuring at 280nm $NO_2$ also absorbs radiation, although to a lesser extent, at this wavelength. Thus, by determining the total absorption occuring at 280nm, and comparing it with that at 540nm, it is possible to correct for or cancel the effect of the $NO_2$ regardless of its concentration.

In a first radiation path or channel, terminating at first photosensor 24, the effect of the $NO_2$ on 540nm radiation is effectively ignored. This is due to the presence of filter 27, which substantially blocks 540nm radiation so that subsequent activity in the channel must be due to the presence of the radiation having a wavelength of 280nm. Nonetheless, since the photosensor elements used are responsive primarily to 540nm radiation it is now necessary to convert the 280nm radiation, whose amplitude reflects the presence of both the $SO_2$ and $NO_2$, if any, back to the 540nm wavelength so that it may be detected by photosensor 24. This function is fulfilled by phosphor element 28. The resulting 540nm radiation, whose amplitude reflects the attenuation of both $SO_2$ and $NO_2$ at a wavelength of 280nm, traverses filter 29 and impinges upon photosensor 24.

At the same time, in a second or "reference" path the radiation issuing from the sample chamber encounters filter 29. This filter allows the 540nm radiation, reflective of the presence of $NO_2$, to pass while attenuating the 280nm and spurious infared radiation. The 540 radiation then traverses filter 30 substantially unattenuated and strikes second photosensor 25. As set forth above, any stray 254nm radiation is selectively absorbed by the mercury vapor which fills the envelope 23.

It will now be understood by those skilled in the art that the relative response of photosensors 24 and 25 may be taken to be indicative of the degree of $SO_2$ present in a given sample, regardless of the presence of absence of $NO_2$. Since the $NO_2$ attenuates the 280 and 540nm radiation substantially equally, it will have an equal effect upon both photosensors 24 and 25 so that differential output therebetween will remain uneffected. However, the presence of $SO_2$ will result in a substantial attenuation of only the 280nm radiation, which effects only photosensor 24. In this manner, the differential between the signals produced by photosensors 24 and 25 will increase, the amount of increase reflecting the degree to which $SO_2$ is present in the sample to be analyzed.

Figure 2:
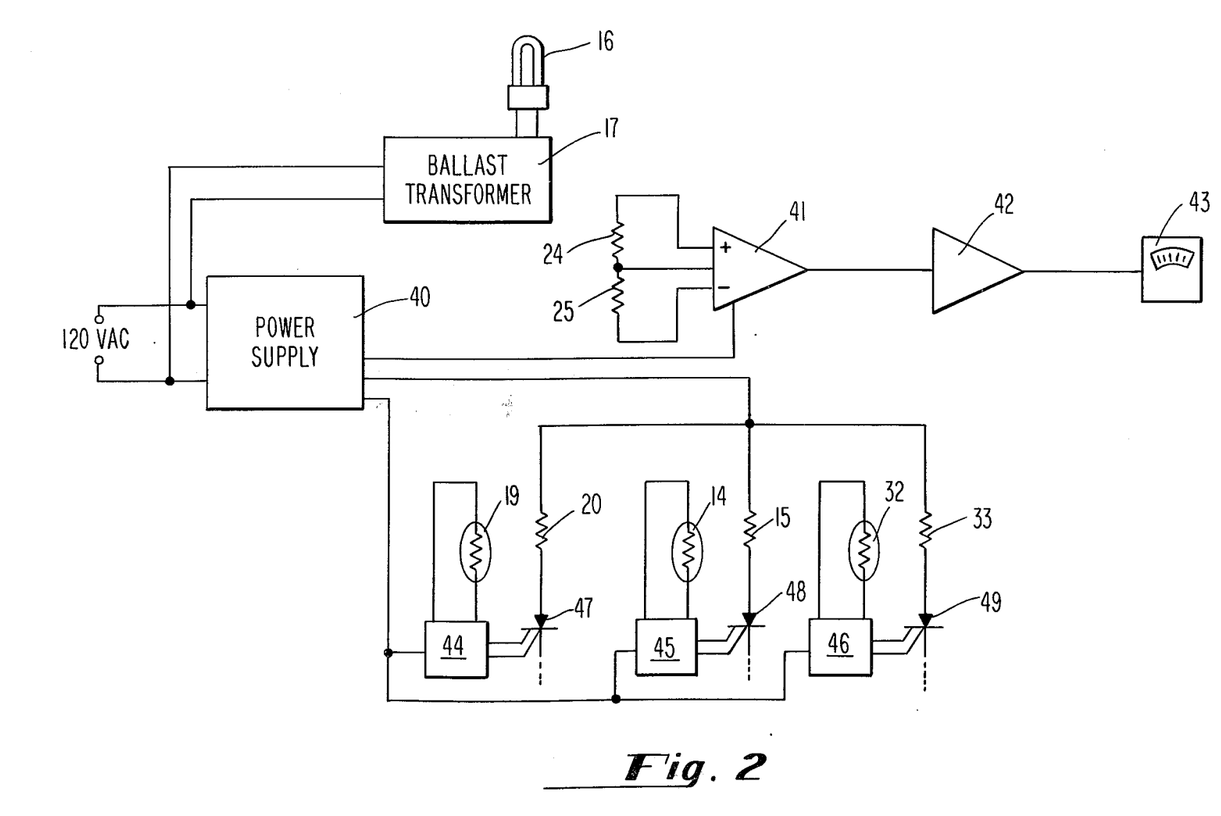
FIG. 2 is a schematic drawing showing the connection of certain electrical elements of the present invention.

Turning now to FIG. 2, there is shown a schematic diagram of elements of the electrical system used in a preferred embodiment of the present invention. A main power supply 40 is adapted to be coupled to a commonly-available source of electrical energy, herein depicted as 120 v. AC current. The power supply may be of several commercially available units, or may easily be fabricated from familiar components. The power supply advantageously takes the form of a transformer having a plurality of secondary windings, the turns ratio of the windings being dependent upon the value of the voltage necessary to drive the various elements of the circuit. A diode bridge coupled across a secondary winding, for instance, gives rise to a rectified DC voltage which may be filtered by means of a shunt capacitor if desired.

The input power may be applied directly to the ballast transformer 17 of lamp 16 in the usual manner, the specifications of the ballast transformer being determined by the type of lamp used, and are ordinarily set forth in the recommendations of the lamp manufacturer. Photocells 24 and 25 are coupled directly to a preamplifier and comparator 41 which is advantageously located in close physical proximity to the photosensors. By avoiding use of a long length of conductor for carrying the unamplified signals from the photosensors to the preamplifier, the introduction of spurious noise signals to the otherwise weak photosensor signal will be avoided. Once amplified by the preamplifier unit 41, the signals are transmitted to the final amplifier 42 which may be disposed at any convenient location. Comparator 41 serves to algebraically combine signals reflecting the responses of photosensors 24 and 25 to impingent radiation, and to output a signal representative of the difference therebetween.

In the illustrated embodiment, the signal from amplifier 42 is applied to a meter 43 which is graduated to indicate the amount of $SO_2$ detected; however, it will be recognized that the signal outputted by the comparator could alternatively be utilized to operate an alarm system, a chart or recording device, or fed back to effect appropriate changes in the process or activity which is producing the $SO_2$-bearing effluent.

Trigger circuits 44, 45 and 46 are coupled to thermistors 19, 14, and 32 respectively. These thermistors, as set forth above with respect to the embodiment of FIG. 1 reflect the temperature of the lamp, sample chamber, and photosensor envelope respectively. The characteristics of the thermal sensing devices thus determine the activity of the triggering circuits and therefore the amount of current passed to the various heating elements.

Current through the heating elements is controlled by appropriate switching means, herein depicted as SCR's 47, 48 and 49. As is known to those skilled in the art, the SCR is in effect a unilateral switched element which can be gated on and commutated at appropriate times to allow predetermined pulses of current to flow through a load.

Suggested circuits for gating and commutating SCR's are published by the manufacturer, many examples being set forth the Silicon Controlled Rectifier Manual, second edition, published by the Rectifier Components Department of the General Electric Co. at Auburn, New York. The frequency and duration of the conductivity of the SCR may thus be constrained to be a function of the sensed characteristic of thermistors 19, 14 or 32. As in the case of preamplifier/comparator 41, appropriate biasing potentials are supplied to the SCR's and gating circuits 44, 45 and 46 by means of power supply 40.

Figure 3:
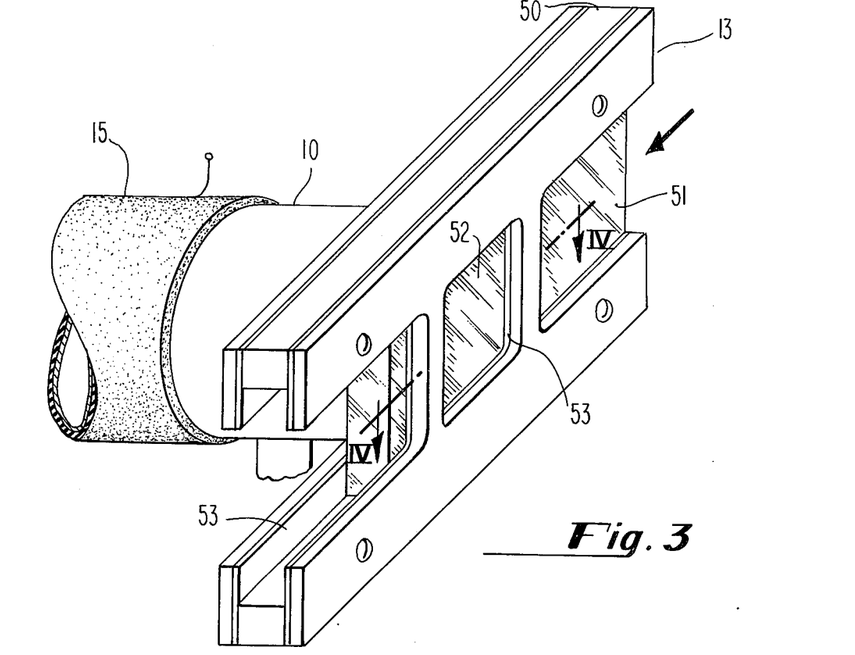
FIG. 3 is a perspective view of a partially disassembled apparatus showing the construction of the window means.

FIG. 3 discloses a partially disassembled spectrophotometer of the type disclosed in FIG. 1 depicting in detail the construction of one of the windows disposed at the ends of sample chamber 10. A frame 50, advantageously fabricated from corrosion resistant metal such as stainless steel, comprises upper and lower generally U-shaped guides or tracks. Slidingly received within the guides is a pane 51 which may be of quartz or other suitable material. An opening 52 is formed in a central section at either side of the frame, providing an aperture through which radiation may pass. The pane 51 is of an extended length which is substantially twice that required to close aperture 52. In this manner, one end of the pane may form a window in the aperture as shown until such time as it accumulates sufficient dirt, smoke, fly ash or other impurities from the samples introduced within aperture 52. The portion of the pane previously used to close the aperture is withdrawn therefrom and exposed so that it may be recleaned if necessary. However, in accordance with the construction hereinafter described such a cleaning operation may be partially or wholly dispensed with.

Extending between pane 51 and frame 50 of the window assembly is a generally flat gasket element 53. Although only that gasket disposed on the far side of the window assembly from the sample chamber is visible in FIG. 3, it will be appreciated that a similar gasket is disposed between the pane and the opposite side of the frame. Although many materials may be used, due to the need to maintain the chamber in a sealed condition the consequent pressure of the gasket material upon the pane makes it highly desirable that a gasket material having a low coefficient of friction be used. While in one successfully tested embodiment the gaskets were formed of Teflon (a proprietary designation for a fluorocarbon plastic material manufactured by the E. I. DuPont deNemours Corp. of Wilmington, Delaware) generally speaking an acceptable gasket may be formed of any suitable fluorocarbon resin or fluoroplastic in accordance with the present invention. Such fluorocarbon plastics or resins include the high molecular weight polymers and copolymers of tetrafluoroethylene, chlorotrifluoroethylene, hexafluoropropylene, and vinylidene fluoride. Further, it is believed possible to employ a mixture of two or more different fluorocarbon resins or fluoroplastics in the formation of a suitable material; and it is contemplated that other suitable fluorocarbon resins useful in the practice of the present invention will readily occur to those skilled in the art.

In order to further assure the proper resilient biasing of gasket 53 against sliding pane 51, a narrow groove is formed about the periphery of aperture 52 at the inner surface of the window frame, and a loop of gasket material such as an O-ring is placed within the groove such that it protrudes slightly therefrom. A cross-sectional illustration of this construction is illustrated at 54 of FIG. 4. With the window means assembled, the O-rings exert force upon the flat gasket elements, causing them to sealingly engage the opposing surfaces of pane 41 and thus assist in maintaining the integrity of sealed chamber 10.

Figure 4:
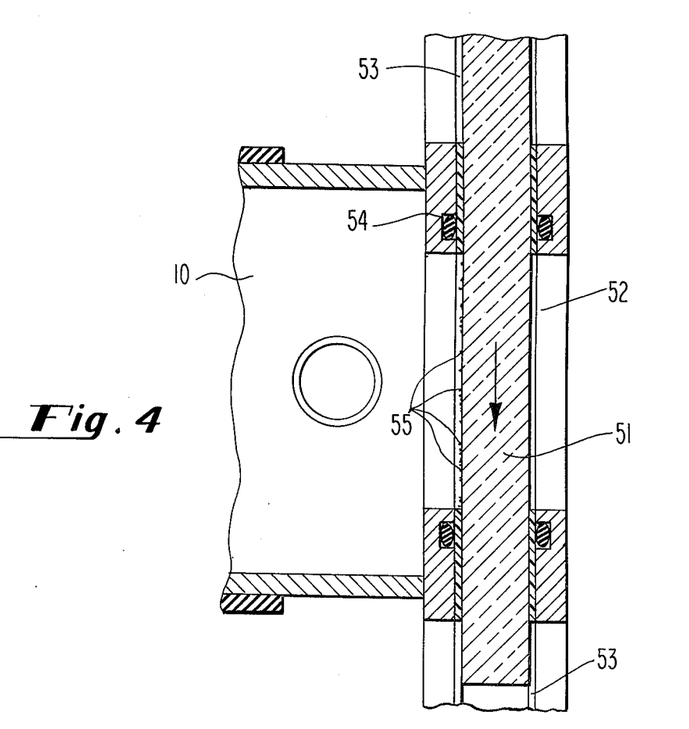
FIG. 4 is a view taken at 4—4 of FIG. 3.

Turning now to FIG. 4, the self cleaning action of the window means assembly is depicted. As the pane 51 is translated in the direction indicated the lower portion of the pane which previously served to close aperture 52, is effectively wiped by opposing gaskets 53. In this manner, particulate material 55 which has accumulate upon the inner surface of the pane is swept to one corner thereof from which position it is dissipated by air currents within the chamber. When the pane in its new position accumulates an undesirable amount of particulate material, the pane is simply slid back to its original position, at which point the wiping action is repeated at the other side of the aperture. The portion of the pane extending within the guides of the frame may further be manually cleaned, although in practice this has usually been found to be unnecessary. In any event, the operation is performed without disturbing the continuity of the seal afforded the sample chamber, and in fact may be accomplished during analysis of a sample with only a momentary discontinuity in the signal outputted by the system.

As will be evident from the foregoing description, certain aspects of the invention are not limited to the particular details of the examples illustrated, and it is therefore contemplated that other modifications or applications will occur to those skilled in the art. It is accordingly intended that the apended claims shall cover all such modifications and applications as do not depart from the true spirit and scope of the invention.

What is claimed is new and desired to be secured by Letters Patent of the United States is:

1. Non-dispersive spectrometric apparatus for detecting the presence of a first gaseous material despite the presence of a second gaseous material, said first gaseous material absorbing electromagnetic radiation at a relatively high rate at a first wavelength, said second gaseous material absorbing electromagnetic radiation at both said first wavelength and at a second wavelength, comprising:

a source of electromagnetic radiation;
first and second photosensor means, said photosensor means being responsive to one of said first or said second wavelengths;
a chamber for receiving a sample to be tested for the presence of the first gaseous material, said chamber being disposed between said radiation source and said photosensor means;
first phosphor means disposed between said radiation source and said chamber for receiving radiation from said source and emitting in response thereto radiation at said first and said second wavelengths;
filter means disposed between said first photosensor means and said chamber for substantially attenuating radiation at that wavelength to which said photosensors are responsive, and passing the other of said wavelengths;
second phosphor means disposed between said first photosensor means and said filter means and responsive to said other of said wavelengths to produce radiation of the wavelength to which said photosensors are responsive; and
means coupled to said first and said second photosensor means for comparing the relative responses thereof to impingent radiation.

2. The invention defined in claim 1, wherein said first and said second wavelengths are in the ultraviolet range of the spectrum.

3. The invention defined in claim 2, further including second filter means disposed between said second phosphor means and said first and said second photosensor means, said second filter means being adapted to selectively pass radiation at the wavelength at which said photosensors are responsive.

4. The invention defined in claim 3, wherein said first gaseous material is $SO_2$ and said second gaseous material is $NO_2$.

5. The invention defined in claim 4, wherein said photosensor means are disposed within a sealed envelope, further including a source of mercury vapor disposed within said envelope; and
heating means for maintaining the temperature within said envelope at a level sufficient so that adequate mercury vapor is present to attenuate radiation occuring at a wavelength of 254nm.

6. The invention defined in claim 5, further including heating means for maintaining said source of electromagnetic radiation and said chamber at predetermined temperatures.

7. The invention defined in claim 2, wherein said chamber is provided with window means at either end thereof, each of said window means comprising a frame and a pane which is substantially transparent to ultraviolet light, at least one of said panes being elongate, and further comprising resilient gasket means between said frame and said pane to seal said chamber and to allow said elongate pane to be displaced transversely with respect to said chamber, said gasket means serving to wipe accumulated impurities from the portion of the window so translated.

8. A non-dispersive spectrometer of the absorption type for detecting the presence of $SO_2$ in a sample regardless of the simultaneous presence of $NO_2$ comprising:

first and second photosensors responsive to ultraviolet light of a first wavelength;
a source of ultraviolet light;
a chamber disposed between said photosensors and said light source for receiving a sample to be analyzed for the presence of $SO_2$, said chamber having windows transparent to ultraviolet light disposed at the ends thereof;
a first phosphor element disposed between said light source and said chamber and responsive to said light source to emit ultraviolet light at said first and at a second wavelength;
the $SO_2$ exhibiting a relatively high degree of absorption at one of said first and second wavelengths and the $NO_2$ exhibiting predictably proportioned degree of absorption at both said first and said second wavelengths;
a filter disposed between said chamber and said first photosensor for attenuating light at said first wavelength and passing light at said second wavelength;
a second phosphor element disposed between said filter and said first photosensor and responsive to light at said second wavelength to produce light at said first wavelength; and
means coupled to said first and second photosensors for outputting a signal representative of the differential response thereof to impingent radiation.

9. The invention defined in claim 8, further including heating means for maintaining said source of ultraviolet light, said chamber, and said photosensors at predetermined temperatures.

10. The invention defined in claim 9, further including second filter means disposed between said phosphor means and said first and second photosensor means, said filter being adapted to selectively pass radiation at said first wavelength.

11. In a spectrophotometer including a chamber for receiving a gaseous sample to be analyzed, a source of radiation to be directed through said sample, and window means disposed in the walls of said chamber for allowing the passage of radiation therethrough, at least one of said window means comprising:

a frame extending generally transversely to the path of said radiation, said frame having an aperture therein to allow the passage of radiation;
a window comprising an elongate pane of radiation-transparent material;
said frame further comprising upper and lower guide means adapted to slidingly receive said pane whereby said pane may be displaced transversely with respect to said chamber so that an area of the pane in registry with said aperture may be succeeded by another area thereof; and
gasket means disposed between said frame and said pane for substantially sealing the interior of said chamber during displacement of said pane.

12. The invention defined in claim 11, wherein said frame is provided with a groove extending about said aperture for receiving a resilient element therein.

13. The invention defined in claim 12, wherein said gasket means comprise a first member disposed in said groove and a second, generally planar member disposed between said frame and said pane, said first gasket element serving to bias said second gasket element against said pane.

14. The invention defined in claim 13, wherein said second gasket element is formed of a fluorocarbon resin having a relatively low coefficient of friction.

15. The invention defined in claim 14, wherein said pane is formed of quartz.

16. A spectrophotometer for the analysis of a sample by identification of the electromagnetic absorption qualities thereof, said spectrophotometer comprising:
 a lamp for providing ultraviolet radiation;
 first heat responsive means in thermal communication with said lamp;
 a first heating element associated with said lamp;
 first control means coupled to said heat responsive means and said first heating element for maintaining said lamp at a predetermined temperature;
 a chamber for receiving a sample to be analyzed, said chamber having window means disposed at the ends thereof to allow ultraviolet radiation to pass through said chamber and said sample;
 second heat responsive means in thermal communication with said chamber;
 a second control means coupled to said second heat responsive means in said second heating element for maintaining said chamber at a predetermined temperature;
 a second heating element associated with said chamber;
 photosensor means responsive to ultraviolet radiation received from said chamber;
 an envelope surrounding said photosensor means;
 a third heating element associated with said envelope; and
 third control means coupled to said third heat responsive means and said third heating element for maintaining said envelope at a predetermined temperature.

17. The invention defined in claim 16, further comprising filter means disposed within said envelope for selectively transmitting ultraviolet radiation.

18. The invention defined in claim 17, further including a source of mercury vapor disposed within said envelope for providing sufficient mercury vapor to effect substantial attenuation of ultraviolet radiation having a wavelength at 254nm.

19. The invention defined in claim 18, wherein said lamp is of the metallic vapor type.

20. A spectrophotometer for determining the presence of a specified gaseous material in a sample comprising:
 a source of electromagnetic radiation producing radiation at desired wavelengths for analyzing the sample, and radiation at at least one additional undesired wavelength;
 photosensor means responsive to impingent radiation at a predetermined wavelength;
 a sample chamber intermediate said radiation source and said photosensor means and having window means therein for allowing radiation to traverse a sample within said chamber;
 an envelope enclosing said photosensor means; and
 a source of metallic vapor disposed within said envelope for saturating the interior of said envelope with said vapor, whereby said vapor selectively absorbs the radiation at said undesired wavelength.

21. The invention defined in claim 20, wherein said metallic vapor is mercury.

22. The invention defined in claim 21, wherein said vapor source comprises a segment of metal, at least the surface of said segment being amalgamated with said mercury.

23. The invention defined in claim 22, further including heat responsive means in thermal communication with said envelope;
 a heating element with said envelope; and
 control means coupled to said heat responsive means and said heating element for maintaining said envelope at a predetermined temperature.

24. The invention defined in claim 23, further including filter means disposed in said envelope for selectively passing ultraviolet radiation at a predetermined wavelength.

25. The invention defined in claim 24, further including a phosphor element disposed within said envelope and responsive to impingent radiation at one wavelength for emitting radiation at another wavelength.

* * * * *

PO-1050
(5/69)

UNITED STATES PATENT OFFICE
CERTIFICATE OF CORRECTION

Patent No. 3,935,463      Dated January 27, 1976

Inventor(s) John Kenneth Jacobsen

It is certified that error appears in the above-identified patent and that said Letters Patent are hereby corrected as shown below:

Column 5, line 54, after "reference" insert the word --to--.

Column 6, lines 1 and 4, change spelling of "occuring" to --occurring--

Column 7, line 42, after "forth" insert the word --in--.

Column 8, line 51, change "accumulate" to --accumulated--.

Column 9, line 4, change spelling of "apended" to --appended--.

Column 9, line 61, change spelling of "occuring" to --occurring--.

Column 12, line 13, delete second "at".

Signed and Sealed this

Twenty-first Day of September 1976

[SEAL]

Attest:

RUTH C. MASON
*Attesting Officer*

C. MARSHALL DANN
*Commissioner of Patents and Trademarks*